(12) United States Patent
Farris

(10) Patent No.: US 6,673,050 B1
(45) Date of Patent: *Jan. 6, 2004

(54) METHOD AND APPARATUS FOR LOADING SYRINGES WITHOUT THE NEED FOR HYPODERMIC NEEDLES

(76) Inventor: Barry Farris, P.O. Box 1990, Pollock Pines, CA (US) 95726

(*) Notice: Subject to any disclaimer, the term of this patent is extended or adjusted under 35 U.S.C. 154(b) by 0 days.

This patent is subject to a terminal disclaimer.

(21) Appl. No.: 09/541,731

(22) Filed: Apr. 3, 2000

Related U.S. Application Data

(62) Division of application No. 08/976,526, filed on Nov. 21, 1997, now Pat. No. 6,045,538.

(51) Int. Cl.⁷ .................................................. A61M 5/00
(52) U.S. Cl. ........................ 604/243; 604/500; 604/185
(58) Field of Search ............................ 215/47–49, 212; 604/216, 217, 234, 236, 256, 259, 408, 412–415, 240–243

(56) References Cited

U.S. PATENT DOCUMENTS

| | | |
|---|---|---|
| 829,178 A | 8/1906 | Stegmaier |
| 1,377,113 A | 5/1921 | Boyle |
| 2,486,321 A | 10/1949 | Sullivan |
| 2,773,521 A | 12/1956 | Persson |
| 3,187,966 A | 6/1965 | Klygis |
| 3,419,007 A | 12/1968 | Love |
| 3,977,553 A | 8/1976 | Cornett, III et al. |
| 4,046,145 A | 9/1977 | Choksi et al. |
| 4,130,117 A | 12/1978 | Van Eck |
| 4,163,509 A | 8/1979 | Amneus |
| 4,213,456 A | 7/1980 | Bottger |
| 4,465,472 A | 8/1984 | Urbaniak |
| 4,643,309 A * | 2/1987 | Evers .......................... 206/364 |
| 4,883,473 A * | 11/1989 | Thomas ....................... 222/107 |
| 4,921,137 A | 5/1990 | Heijenga |
| 4,944,736 A | 7/1990 | Holtz |
| 5,018,646 A * | 5/1991 | Billman et al. .............. 222/107 |
| 5,035,689 A * | 7/1991 | Schroeder .................... 604/414 |
| 5,201,751 A | 4/1993 | Cohen |
| 5,222,948 A | 6/1993 | Austin et al. |
| 5,261,881 A | 11/1993 | Riner |
| 5,334,173 A | 8/1994 | Armstrong, Jr. |
| 5,374,263 A | 12/1994 | Weiler |
| 5,409,125 A | 4/1995 | Kimber et al. |
| 5,716,346 A * | 2/1998 | Farris .......................... 604/236 |
| 6,045,538 A * | 4/2000 | Farris .......................... 604/243 |

FOREIGN PATENT DOCUMENTS

| | | |
|---|---|---|
| EP | 0 324 257 A2 | 7/1989 |
| EP | 0 350 772 A1 | 1/1990 |
| FR | 259 4687 A | 2/1986 |

* cited by examiner

*Primary Examiner*—Manuel Mendez
(74) *Attorney, Agent, or Firm*—Bernhard Kreten

(57) ABSTRACT

A needleless dosage transfer system for filing medicating devices such as syringes or needleless cannulas to minimize the likelihood of an unwanted needle stick and to avoid the initial cost of a needle as well as the disposal cost of the needle. A vial has a body portion 20 formed with flexibly deformable walls and defines a blind bore. An opening of the vial includes a tapered section adapted to frictionally fit over a taper of a male luer-type fitting commonly found on syringes and needleless cannulas. By deforming the walls of the vial, fluid is forced from the vial into a syringe. The opening of the vial 10 is protected with a cap and includes a scoreline which, when fractured, defines the opening. The cap to be removed from the vial prior to its use is fabricated as one piece with the vial in order to assure sterile conditions during manufacture and filling. A tab is associated with the cap which lists the ingredients within the vial. The vial also supports an area which lists the vial's contents. The cap is structured with a coupling so that after its removal from the vial, it can frictionally engage the luer opening of the syringe or cannula. The tab provides indicia thereon as to the contents within the thus loaded syringe and to temporarily seal the syringe or cannula.

5 Claims, 3 Drawing Sheets

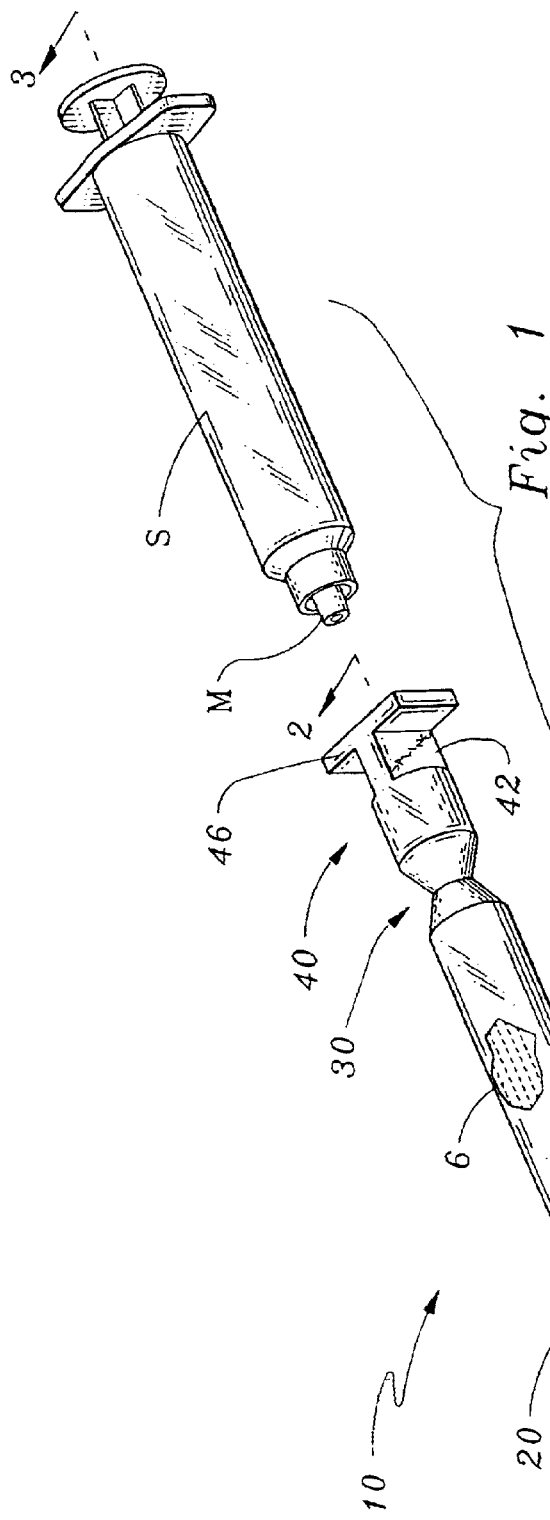
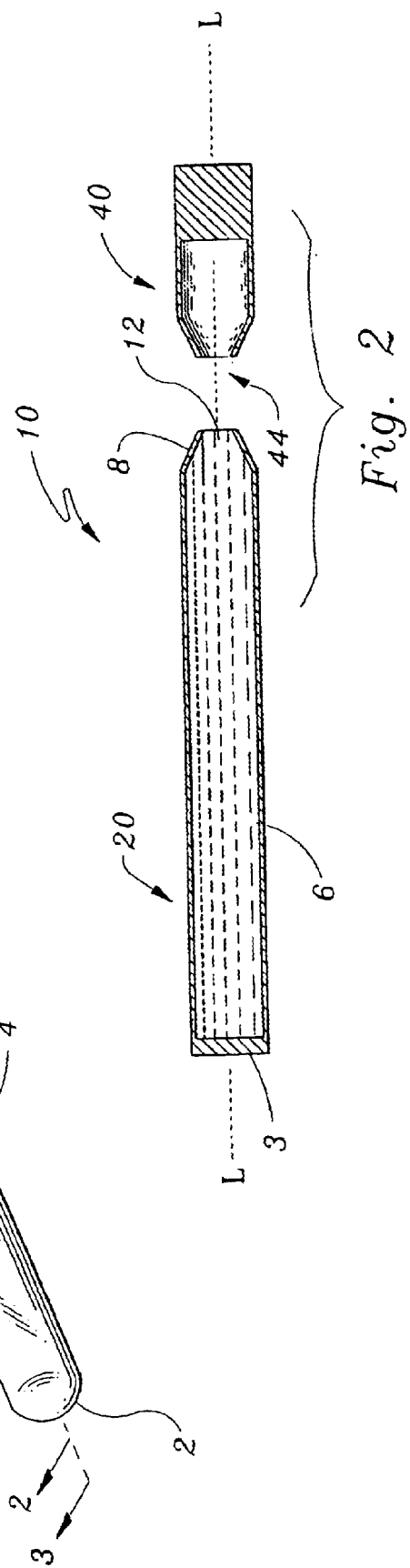

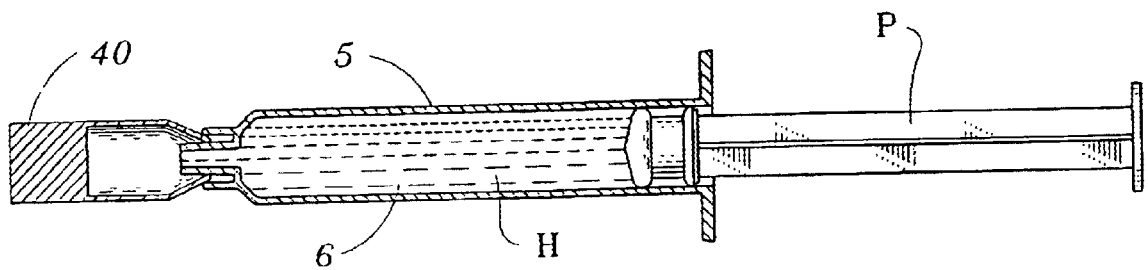
Fig. 5
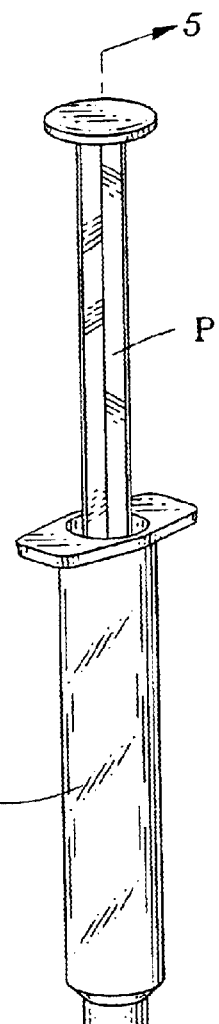
Fig. 6
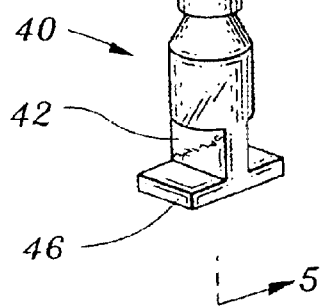

METHOD AND APPARATUS FOR LOADING SYRINGES WITHOUT THE NEED FOR HYPODERMIC NEEDLES

This application is a division of application Ser. No. 08/976,526 filed Nov. 21, 1997 now U.S. Pat. No. 6,045,538.

FIELD OF THE INVENTION

The following invention relates generally to a method and apparatus for transferring fluid from an ampule or vial into a syringe or cannula without the need for a needle. More specifically, a male and female docking arrangement is disclosed coupled with structure for storing and transferring liquids so that the number of times needles are used in a medicating situation is kept to a minimum.

BACKGROUND OF THE INVENTION

Diseases such as hepatitis and AIDS, which are pathogens that can be transmitted with the body fluids of a person, are running rampant globally. As a result, medical environments such as hospitals spend considerable amounts of money, time and energy attending to the problems that arise when hypodermic needles are required.

Complex protocols are evolving which attempt to minimize the likelihood of a needle stick from the time that a needle has been removed from its sterile storage environment through loading, utilization and disposal. Examples of heightened care with respect to the use of hypodermic needles are chronicled in patent literature, in the development of anti-stick needle caps, devices which destroy the needle itself after use and other instrumentalities for receiving both the used needle and syringe for safe disposal. Thus, the prevailing systems are based on the premise of the very existence of the needle for the medicating process.

The instant invention to a large extent obviates the need for the needles themselves in the many common instances where syringe needles have heretofore been used. Typically, one scenario where the use of a hypodermic needle is now commonplace includes the steps immediately prior to injection in the patient. The process involves loading the syringe with a sterile, pharmaceutical-grade fluid by extracting medicating fluid from a vial by using the needle of a syringe for access. When using an ampule, the tip is broken off and then the ampule is entered with a needle, often a filtered needle to filter out glass particles. Next, penetrating the skin of the patient who is to receive this medicating fluid is sometimes performed with the same, or another new, needle.

Prior art drug containing vials are formed from an open mouthed bottle or jar wherein the walls of the container defining the vial are rigid and non-flexible. The opening of the jar includes a lip which supports a metal ferrule which supports an elastomeric diaphragm made from a rubber-type material having a resealable property such that once the diaphragm has been penetrated by a needle and then removed, the diaphragm reseals itself. Examples of these devices are believed to be presently classified in class 604, subclass 415. Typically, a syringe body is first fitted with a hypodermic needle. It is common practice that prior to the needle being plunged into the vial through the rubber diaphragm, it is first loaded with air. Because the prior art vials are rigid, the vial is first pressurized to assist in fluid withdrawal. While this technique makes it easier to withdraw fluid, it introduces non-sterile air into the vial. Technically, the needle is to then be replaced with a new needle for injecting a patient.

The syringe is, in general, an elongate cylindrical object having a plunger adapted to reciprocate within an interior hollow. By withdrawing the plunger from the interior of the cylindrical hollow, fluid is drawn from the vial and is loaded into the syringe. Once the syringe has been removed from the vial, great care must be exercised for a multiplicity of reasons. The medication contained within the syringe is now provided with the present ability to discharge the medication to any who come in contact with the needle, albeit inadvertently. In order to reduce the amount of time a "loaded" syringe is carried, the medicating healthcare professionals normally will use a cart which contains all pharmaceuticals which are to be distributed during rounds to the patients. This reduces the amount of time the healthcare professional is required to walk with an armed syringe whose needle has been exposed or whose exposed needle has been recapped. Recapping provides further risk of self sticking due to misaligning a needle cap with the syringe.

After dispensing the medicine to the patient, the healthcare professional typically has one of several choices, none of which is entirely satisfactory for safe disposal of the needle. In one scenario, the healthcare professional is required to carefully recap the needle hoping that in the multiple times this procedure is reperformed he or she does not misalign the cap with the needle and inadvertently suffer a needle stick.

Another device has been developed which appears like a pencil sharpener and allows the healthcare professional to place the leading end of the syringe into an opening where an electric current is applied to the needle which melts the needle.

A third strategy involves discarding the needle and the syringe in a container for subsequent destruction or internment as biomedical waste. This technique presents ongoing risk to people who subsequently handle this waste.

The Food and Drug Administration (FDA) has accordingly issued an alert urging hospitals to use needleless systems or recessed needle systems instead of hypodermic needles for accessing Intravenous lines. Plastic cannulas now exist which can fit onto luer connections and penetrate:sealable diaphragms on infusion catheters. Thus, the FDA is urging the use of hypodermic needles only to penetrate the skin.

SUMMARY OF THE INVENTION

The instant invention completely avoids the use of a needle when loading the syringe by extracting fluid from a vial or ampule. In its essence, the instant invention takes advantage of a coupling that is the standard on a majority of syringes which had heretofore only been used in the past to support the hypodermic needle on the syringe. This coupling, called a luer fitting, has a male component and a female component. Typically, the syringe is configured with the "male" luer coupling which appears as a truncated cone that has an opening at its narrowest cross section. The luer coupling diverges toward an interior cylindrical hollow portion of the syringe. The instant invention replaces the "female" luer coupling and associated needle itself and instead replicates the female coupling on a specially formed ampule or vial so that docking between the ampule and a needleless syringe benefits from the pre-existing male coupling already found on common syringes. Walls of the ampule or vial are flexible to promote removal of the fluid therewithin.

With an opening of the ampule and the opening of the syringe in face-to-face docking registry and in fluidic communication, the ampule can be evacuated by any of a combination of manipulative steps. First, assume the syringe is in its initialized state, with its plunger nested well within the cylindrical hollow of the syringe body so that the plunger is in a compact, retracted state. The contents of the ampule can then be transferred with a minimal amount of air into the syringe by deforming the side walls of the ampule and "milking" (i.e. applying hydrostatic force to) the liquid from the ampule and thus into the syringe. This causes the plunger of the syringe to translate outside the cylindrical hollow. As the plunger advances out of the cylindrical hollow, liquid enters the syringe.

Another strategy involves manipulation of the plunger to draw the fluid from the ampule by suction so that the arming of the syringe occurs by retracting the plunger to extract the liquid from the ampule. As before, the plunger starts well within the syringe and reciprocates outwardly of the cylindrical hollow.

A third strategy is a hybrid of the two previously discussed techniques which involves manipulation of both the ampule by squeezing the ampule and suction by moving the plunger out of the syringe cylindrical hollow. Thereafter, in all cases the ampule is disconnected from the syringe.

Once the ampule has been removed, a syringe has the intended fluid medication disposed therewithin. Unlike the prior art, no needle has yet been involved. Also, no air from the ambient environment has been mixed with the sterile fluid as was the case with rigid wall vials.

In one form of the invention, it is contemplated that the opening associated with the ampule is provided with a removeable cap having a luer-type coupling and an indicia bearing tab. The medicinal contents of the ampule is stamped on the tab for identification purposes. With such an arrangement, it is possible to transfer the cap and tab from the ampule and connect the cap to the syringe to provide a tell tale of the contents of the fluid contained within the syringe. As an alternative, the ampule could remain docked to the syringe until subsequent use. The ampule would also note the contents on a surface thereof.

As a result of this system, the entire process for filling a syringe has been accomplished without the use of a needle. Personnel are able to operate more quickly with less fear of either inadvertent needle stick or inadvertent exposure to the medicine contained within the syringe.

It is to be noted that for many in patients, the standard procedure in a hospital is to tap into a person's vein only once with an infusion catheter and to leave the catheter needle in place with tubing communicating therewith so that subsequent fluids such as intravenous drips and the like can be used. With such a system, a needle would never be needed with the syringe according to the present invention. "Y" connectors are well known in the art, one branch of which would have a complemental female luer coupling. Thus, for a patient's entire stay at a hospital, the only needle associated with that one patient, ideally, would be the one which initially had been placed in the patient's vein to support the infusion catheter. In this way, the opportunity for inadvertent needle sticks would be reduced to a minimum.

OBJECTS OF THE INVENTION

Accordingly, it is a primary object of the present invention to provide a method and apparatus for transferring sterile fluid from an ampule to a hypodermic syringe without the need of a hypodermic needle.

It is a further object of the present invention to provide a device and method as characterized above which reduces the amount of time which hospital staff must spend in transferring fluid from a sterile ampule to a hypodermic syringe while also eliminating the fear of an inadvertent needle stick thereby avoiding the possibility of both unwanted contamination and unwanted medication.

A further object of the present invention contemplates providing a device and method as characterized above which is extremely inexpensive to fabricate, safe to use and lends itself to mass production techniques.

A further object of the present invention is to provide a device which can reduce the number of times that needles are required in a hospital or other medical setting.

A further object of the present invention contemplates providing a device and method which minimizes the disposal problems of hypodermic syringes with needles.

A further object of the present invention contemplates providing a device and method for use in which a telltale is associated with first the ampule that stores the medicine, and then the syringe so that the fluid transferred from the ampule and into the syringe will be known at all times. In this way, the chain of custody of the fluid can be more readily monitored.

A further object of the present invention contemplates providing a system for loading syringes that obviates the need for the medicating health professional from having to trundle a miniature pharmacy on a cart from patient to patient. By pre-filling the syringes at a remote location added security and efficiency may be provided.

When viewed from a first vantage point it is an object to provide a needleless dosage transfer system for removing a sterile fluid from a sealed vial to a conventional syringe. The syringe has a plunger such that the plunger of the syringe translates from a first position telescoped within an interior cylindrical hollow of the syringe to a second position where the plunger has been displaced from the interior hollow and replaced by the fluid. The vial is defined by an end, collapsible sidewalls extending from the end thereby defining a blind bore and having an open end, a coupler at the open end of the vial, and a removable cap occluding the open end at the coupler. The vial coupler is provided with means to connect to a needleless opening of the syringe to be in fluid communication therewith, whereby fluid can be transferred to the syringe from the vial without an interconnecting needle.

Viewed from a second vantage point, it is an object to provide a method for transferring injectable fluids from a storage ampule or vial to a needleless syringe or other device using a male luer fitting. The syringe has a first coupling and an opening which communicates within an interior cylindrical hollow of the syringe so that fluid passes by the first coupling through the opening and into the hollow to load the syringe. The steps include providing a vial filled with fluid and with an outlet which has a second coupler defining the outlet. The vial is sealed by occluding the coupler outlet with a cap Subsequently, removing the cap and orienting the first and second couplers into complemental fluid tight docking arrangement (so that the opening of the vial registers with the opening of the syringe) allows transfer of the contents of the vial to the syringe without the need for a traditional needle extraction system.

Viewed from a third vantage point, it is an object to provide a method for forming an ampule to transfer medicine to be injected. The steps include forming an ampule with resilient walls so that the ampule can be collapsed, forming an opening on the ampule such that the opening is circumscribed by a coupler which is complementally fashioned to receive a dose administering device, filling the ampule with the medicine and finally capping the ampule opening.

These and other objects were made manifest when considering the following detailed specification when taken into conjunction with the appended drawing figures.

BRIEF DESCRIPTION OF THE DRAWINGS

FIG. 1 is a perspective view of the apparatus according to the present invention shown adjacent an empty syringe prior to docking with the syringe.

FIG. 2 is a sectional view of the vial of FIG. 1 having had an end cap removed to facilitate docking.

FIG. 5 shows a sectional view of the syringe of FIG. 4 removed from the vial and with the safety cap of the vial occluding the outlet of the syringe for subsequent use.

FIG. 6 shows a perspective view of the syringe and safety cap oriented so that the syringe can stand on a supporting foot of the safety cap, or prevent rolling of the syringe when placed on a flat surface.

DESCRIPTION OF PREFERRED EMBODIMENTS

Figure 3:
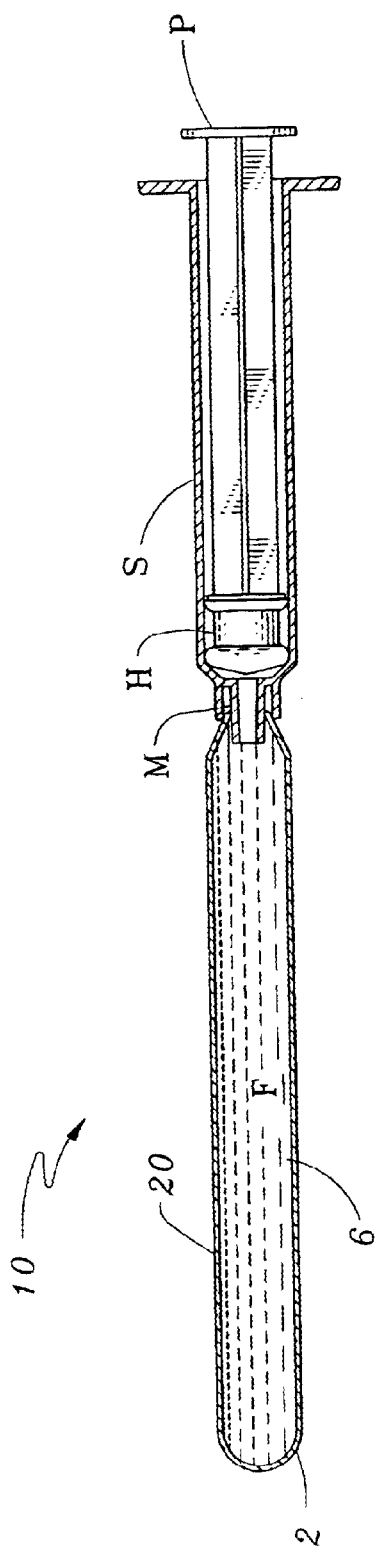
FIG. 3 is a sectional view showing the vial and the syringe in docking orientation where a coupler associated with the vial is in frictional engagement with a coupler associated with the syringe, where a plunger of the syringe is nested within the syringe's body.

Referring to the drawings now, wherein like reference numerals refer to like parts throughout the various drawing figures, reference numeral 10 is directed to the vial or ampule according to the present invention.

In its essence, the vial 10 is formed from two parts: a body portion 20 and a cap portion 40. An area of transition noted as a scoreline 30 serves as an area of demarcation between the cap 40 and body 20. The scoreline 30 allows the cap 40 to be dissociated from the body 20 so that the body 20 can dock with a syringe S as shown in FIG. 3 for filling the syringe S with a fluid F contained within the body 20 of the vial 10.

More specifically, and referring to the drawings in detail, the vial 10 includes a body 20 having an end wall 2, and a peripheral side wall 4. The peripheral side wall 4 has one proximal end coterminus with an outer periphery of the end wall 2 and extends away from the end wall 2 so that a blind bore 6 has been formed within which the fluid F is to be stored. As shown, the side wall 4 can be substantially cylindrical in shape. The end wall 2 can be hemispherical. Alternatively, the end wall 2 can appear as a fan-shaped seam 3 caused by flattening and sealing the sidewalls 4 (See FIG. 2).

Typically, fluids such as a saline solution or pharmaceutical drugs and other medicaments can be stored within the blind bore 6. A distal end of the side wall 4 remote from the end wall 2 is provided with a tapering section 8 which converges towards a longitudinal axis L of the vial .10 defining a converging portion of the vial 10. This tapering section 8 converges to an opening 12, or outlet and thereafter communicates with the cap 40. The opening 12 defines a coupler of the vial 10. The area of transition where the opening 12 is located is preferably coincident with the scoreline 30 to facilitate fracture of the vial 10 at the opening 12. Thus, the cap 40 can be separated from the body 20.

The cap 40 includes a flag type tab 42 on an exterior surface thereof upon which is printed the product contained within the vial 10. The tab 42 is shown having a substantially rectangular, planar configuration to provide an exposed surface sufficient to place the name of the product on the tab. The tab 42 also serves as a purchase area to allow a person to grasp the cap 40 so that a twisting motion of the cap 40 with respect to the body 20 will cause severing of the body 20 from the cap, 40 at the scoreline 30.

The cap 40 also includes an interior passageway 44 having a diverging contour 38 which substantially mirrors the slope of the tapered section 8 of the body 20 of the vial 10 about an axis of symmetry coincident with the scoreline 30. This diverging passageway 44 extends a short distance within the cap. 40 for purposes to be assigned.

As shown in FIG. 2, prior to docking with the empty syringes S (or needleless cannula), the cap 40 will have been removed from the body 20 of the vial 10. This allows the opening 12 of the body 20 to be exposed. The opening 12 has an inner peripheral dimension complemental to an exterior diameter of a male luer coupling M found on the syringe's or cannula's outlet. This coupling M defines an opening which forms a coupler of the syringe. Typically, this luer-type connection tapers and diverges, as it approaches a cylindrical hollow H of the syringe S.

For a friction fit, and with respect to the syringe S shown in FIG. 1, the taper of the luer M traditionally couples to a needle. Instead, the syringe docks with the vial 10 as shown in FIG. 3 such that the "male" conical taper of luer coupling M of the syringe S passes within the female opening 12 of the body 20 and becomes frictionally engaged in the tapering section 8 of the vial's body 20. Note that the plunger P on the syringe S (FIG. 3) is in a contracted position such that the syringe's cylindrical hollow H, located on an interior portion of the syringe S has received the plunger P to its entire extent and the push rod of the plunger P is in a position immediately adjacent to the cylindrical barrel of the syringe S. In other words, the syringe S is empty.

Figure 4:
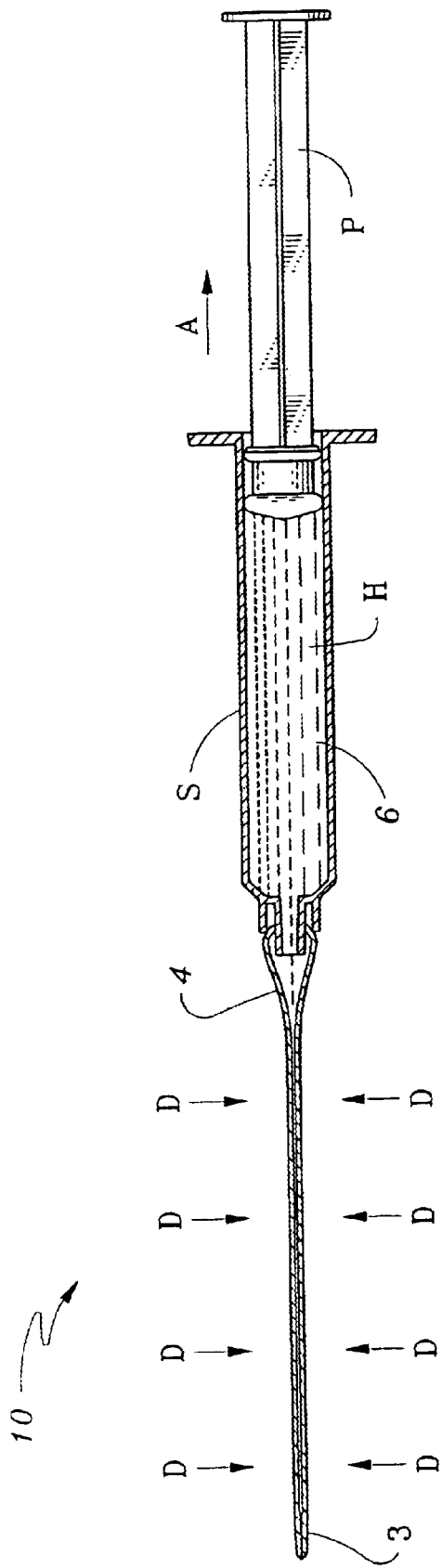
FIG. 4 shows in section the vial having been collapsed so that its fluidic contents have been transferred to the syringe which now has its associated plunger in an extended, deployed configuration.

With respect to FIG. 4, it should be noted that the side walls 4 of the vial 10 are formed from a material having the ability to elastically deform in the presence of force. In other words, the side walls 4 of the body of the vial 10 can collapse. In this way, fluid F contained within the vial 10 can be transferred into the syringe S. It is contemplated that one of three methods could be used to transfer the fluid F of the vial 10 into the syringe S.

One scenario, shown in FIG. 4, envisions the vial 10 being deformed by providing external force in the direction of the arrows D along the outer periphery of the side walls 4. This causes the incompressible fluid F to be forced from the vial 10 and into the syringe S. The plunger P will now be forced by fluidic pressure, induced from the vial 10, to move the plunger P from a first contracted position (FIG. 3) to a second expanded position (FIG. 4). The cylindrical hollow H of the syringe S receives the fluid F. In other words, the syringe S will now have been filled with the fluid F and the plunger P will have been extended to a second position for delivery to a patient.

A second scenario involves docking the syringe S or needleless cannula with the vial 10 as described above. Rather than exerting force D on the vial 10, instead the plunger P is pulled in the direction of the arrow A and causes negative pressure to exist in the cylindrical hollow H of the syringe S. Since the side walls 4 of the vial 10 are elastically deformable, the pressure induced by pulling the plunger P in the direction of the arrow A will cause the fluid F within the vial 10 to migrate into the cylindrical hollow H of the syringe S, filling the syringe S.

A third scenario involves a hybridization of the first two mentioned techniques. Namely, force D on the exterior side walls 4 of the vial 10 will be coupled in concert with pulling of the plunger P in the direction of the arrow A so that the incompressible fluid F will have migrated from the vial 10 to the syringe S.

FIG. 5 is directed to a final manipulation of one component of the apparatus according to the present invention. The cap 40 has indicia thereon correlative to the identity of the fluid F which has now been transferred from the vial 10 into the syringe S. The cap 40 has an interior passageway 44 which is placed in axial registry with the long axis L of the syringe S or needleless cannula. Thus, the syringe S or cannula will be covered with cap 40. As mentioned above, the scoreline 30 of the opening 12 defines an axis of symmetry between the tapering section 8 of the vial body 20 and the diverging contour 38 of the passageway 44 of the cap 40. As shall now be evident, the cap 40 can be frictionally forced over the conical taper of the syringe S thereby covering the male luer coupling M.

In this way, after the syringe S is loaded and ready for subsequent use, the contents of the fluid F within the syringe S will be known to the person dispensing the medication. Thus, different fluids can be pre-loaded into several syringes in a secure area. The healthcare professional can merely take a collection of the syringes or needleless cannulas to the site for ultimate medicating without having to use a drug preparation cart as is commonly in vogue today. The cap 40 can include a support foot 46 to support the syringe S or vial 10 on end. The foot 46 is located at an end of the cap 40 remote from passageway 44 and defines a planar surface transverse to the long axis 2. This allows the on end orientation of FIG. 6. The foot 46 is preferable faceted at extremities thereof so that the foot 46 prevents the syringe S or vial 10 connected thereto from rolling when oriented as shown in FIGS. 1 and 5.

As had been mentioned briefly hereinabove, many people residing in hospitals as in-patients have infusion catheters operatively coupled at all times during their stay. Many of the infusion catheters include a female luer coupling similar to the contour of both the vial 10 and the passageway 44 of the cap. When this is the case, the syringe S never needs to include a needle on the male luer coupling M. Instead, one can administer the medicine directly through the infusion catheter. In this way, the number of instances where trained medical personnel are exposed to administering fluids with hypodermic needles will be minimal. This reduces the amount of time and care required in the efficient performance of their tasks and minimizes both occasions for needle sticks and problems of needle disposal.

Moreover, having thus described the invention, it should be apparent that numerous structural modifications and adaptations may be resorted to without departing from the scope and fair meaning of the instant invention as set forth hereinabove and as defined hereinbelow by the claims.

I claim:

1. A method for transferring injectable fluids from a storage vial to a needleless syringe or the like where the syringe is configured with a first coupler and an opening which communicates within an interior cylindrical hollow of the syringe so that fluid passes by the first coupler through the opening and into the cylindrical hollow and passes fluid into the syringe, the steps including:

providing a vial which has been filled with a fluid, which has an outlet including a second coupler defining the outlet and which has been sealed by occluding the second coupler outlet with an integrally formed cap adjacent the outlet with a scoreline between the outlet and the cap, subsequently removing the cap, wedging the first coupler of the syringe and said second coupler of said vial, respectively into complemental, fluid-tight locking engagement so that the opening of said vial tightly overlies the opening of the syringe, and transferring the contents of the vial to the syringe while the vial collapses.

2. A needleless dosage transfer system, for removing a sterile pharmaceutical grade fluid from a sealed vial to a needleless syringe, comprising in combination, a vial defined by an end and collapsible side walls extending from said end thereby defining a blind bore and an open end which forms a truncated cone, defined by a succession of narrowing circular cross-sections tapering and converging towards said open end, said side walls and open end formed from resilient, collapsible and distendable material, a coupler at said open end of said vial, and a removeable cap integrally formed with said vial and occluding said open end, said vial coupler configured and provided with means to overlie an opening of the syringe in fluid communication therewith by wedging a circular terminus at an end of said converging portion of said vial opening over a circular portion on a diverging portion of the syringe, whereby fluid can be directly transferred from a vial without an interconnecting needle after removing said cap and coupling said open end to an opening of the needleless syringe.

3. A method for transferring injectable fluids from a storage vial to a needleless syringe or cannula where the syringe is configured with a first coupler and an opening which communicates within an interior cylindrical hollow of the syringe so that fluid passes by the first coupler through the opening and into the cylindrical hollow and fills the syringe or cannula, the steps including:

providing a vial which has been filled with a fluid, which has an outlet including a second coupler defining the outlet having a conical taper which narrows towards a longitudinal centerline of the vial and which has been sealed by occluding the second coupler outlet with a cap, subsequently removing the cap, orienting the first and second couplers of, the syringe or cannula and vial, respectively into complemental, fluid-tight locking engagement so that the opening of the vial registers over the opening of the syringe or cannula by a circular end of the conical taper girding the first coupler, and transferring the contents of the vial to the syringe or cannula.

4. A method for forming an ampule to transfer pharmaceutical grade fluid to be administered, the steps including, forming an ampule with resilient walls so that the ampule can be collapsed, forming an opening on the ampule such that the opening is circumscribed by a coupler which is to be complementally fastened to receive a dose administering device where the coupler is configured as having a taper which narrows towards a longitudinal centerline of the ampule, filling the ampule with the pharmaceutical grade fluid, and sealing the ampule.

5. A needleless dosage transfer system, for removing a sterile pharmaceutical grade fluid from a sealed vial to a needleless syringe or needleless cannula, comprising in combination, a vial defined by an end and collapsible side walls extending from said end thereby defining a blind bore and an open end, said side walls formed from resilient, collapsible material, a coupler at said open end of said vial where the coupler is configured as having a taper which narrows towards a longitudinal centerline of the ampule, and a removable cap occluding said open end, said vial coupler configured and provided with means to connect to an opening of the syringe or needleless cannula in fluid communication therewith, whereby fluid can be directly transferred from a vial without an interconnecting needle after removing said cap and coupling said opening to the needleless syringe or cannula.

* * * * *